United States Patent [19]

Martin et al.

[11] Patent Number: 4,526,891
[45] Date of Patent: Jul. 2, 1985

[54] SUBSTITUTED ALKYL AMINE DERIVATIVES OF 6,11-DIHYDRO-11-OXODIBENZ[B,E]OXEPINS

[75] Inventors: Lawrence L. Martin, Lebanon; Linda L. Setescak, Somerville, both of N.J.

[73] Assignee: Hoechst Roussel Pharmaceuticals Inc., Somerville, N.J.

[21] Appl. No.: 474,106

[22] Filed: Mar. 10, 1983

[51] Int. Cl.³ .................. A61K 31/495; C07D 405/06
[52] U.S. Cl. .................... 514/253; 514/278; 514/319; 514/450; 544/375; 546/20; 546/190; 549/354
[58] Field of Search .................. 544/375; 546/20, 190; 549/354; 424/250, 267, 278

[56] References Cited

U.S. PATENT DOCUMENTS

| | | | |
|---|---|---|---|
| 4,107,322 | 8/1978 | McFadden et al. | 424/278 |
| 4,205,170 | 5/1980 | Fujimoto et al. | 549/354 |
| 4,282,365 | 8/1980 | Rokach et al. | 549/354 |

FOREIGN PATENT DOCUMENTS

| | | |
|---|---|---|
| 2435613 | 2/1975 | Fed. Rep. of Germany . |
| 1476214 | 6/1977 | United Kingdom . |
| 1481866 | 8/1977 | United Kingdom . |
| 1538775 | 1/1979 | United Kingdom . |
| 1582191 | 12/1980 | United Kingdom . |

OTHER PUBLICATIONS

Yoshioka et al., "J. Med. Chem.", vol. 21(7), 1978, pp. 633-639.
Ueno et al., "J. Med. Chem.", vol. 19(7), 1976, pp. 941-946.
Derwent, B 26, Sec. C, No. 04662x/03=su-622-403.

Primary Examiner—Richard L. Raymond
Assistant Examiner—James H. Turnipseed
Attorney, Agent, or Firm—Jerome Rosenstock

[57] ABSTRACT

This invention relates to compounds of the formula:

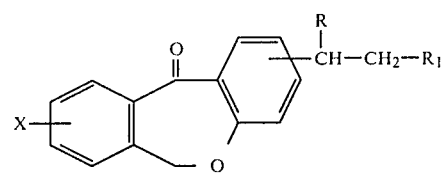

where X is hydrogen, halogen, lower alkoxy, lower alkyl, nitro, hydroxyl and $CF_3$; R is H, and lower alkyl, $R_1$ is $CH_3SO_3$ and

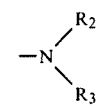

where $R_2$ and $R_3$ are the same or different and are hydrogen, lower alkyl, mesyl ($CH_3SO_2-$), and cycloalkyl loweralkyl;

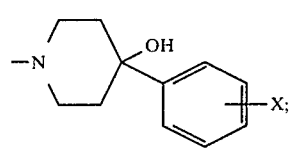

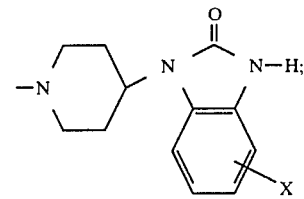

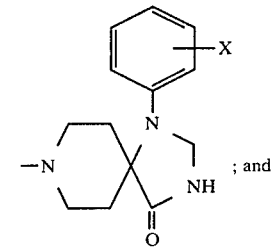

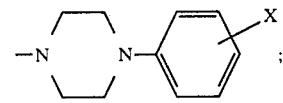

27 Claims, No Drawings

SUBSTITUTED ALKYL AMINE DERIVATIVES OF 6,11-DIHYDRO-11-OXODIBENZ[B,E]OXEPINS

To the best of our knowledge the compounds of the present invention have not heretofore been described of suggested.

The compounds of the present invention have the general formula:

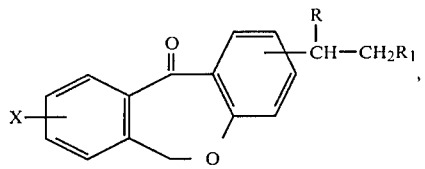

where X is hydrogen, halogen, lower alkoxy, lower alkyl, nitro, hydroxyl and $CF_3$; R is hydrogen, and lower alkyl; $R_1$ is $CH_3SO_3$ and

where $R_2$ and $R_3$ are the same or different and are hydrogen, lower alkyl, mesyl ($-SO_2CH_3$), and cycloalkylloweralkyl;

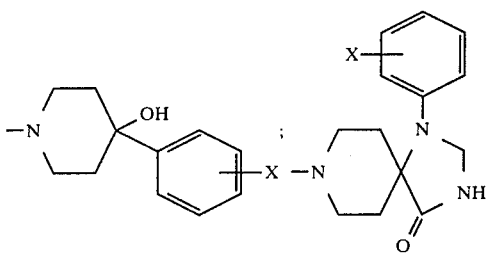

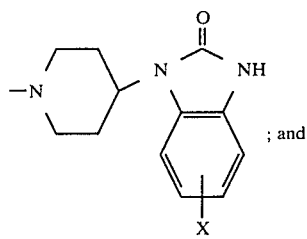

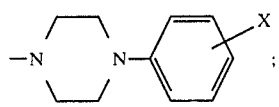

and the pharmaceutically acceptable acid addition salts thereof.

Particularly preferred compounds of the invention are compounds I where R is $CH_3$, and $R_1$ is

In the above definitions and as used hereinafter, the term "lower" means the group it is describing contains 1 to 6 carbon atoms. The term "alkyl" refers to a straight or branched chain hydrocarbon containing no unsaturation, e.g., methyl, isopropyl, tert-butyl, etc. The term "alkoxy" refers to a monovalent substituent which consists of an alkyl group linked through an ether oxygen having its free valence bond from the ether oxygen. The term "halogen" refers to a member of the family consisting of fluorine, chlorine, bromine and iodine. The term "mesyl" means $-SO_2CH_3$. The term "cycloalkylloweralkyl" refers to a monovalent substituent consisting of a saturated hydrocarbon possessing at least one carbocyclic ring of 3 to 7 carbon atoms, e.g. cyclopropyl, cyclobutyl, cyclopentyl, cyclohexyl, cycloheptyl, etc., having its free valence bond from a carbon of the carbocyclic ring.

The compounds of the present invention are prepared in the following manner. The substituents X, R, $R_1$, $R_2$ and $R_3$ are defined above unless indicated otherwise.

A. A substituted (6,11-dihydro-11-oxodibenz[b,e]oxepin-2-yl)ethanol of the formula

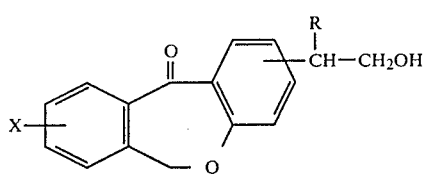

is selected. Compound II is typically prepared from a 6,11-dihydro-11-oxodibenz[b,3]oxepin acetic acid having the formula

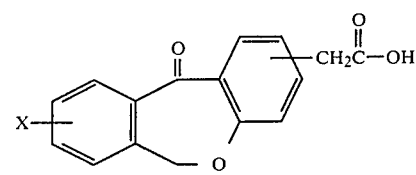

or an α-substituted acetic acid having the formula

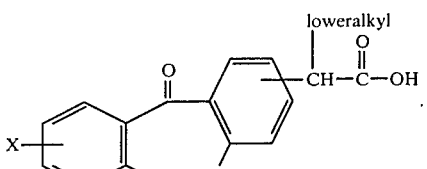

Such acetic acids III may be typically prepared in the general manner described in British Patent Specification No. 1,481,866, and British Patent Specification No. 1,538,775, incorporated hereinto by reference. For example, typically a compound of the general formula (V),

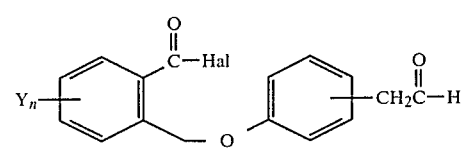

is reacted with a Friedel-Crafts catalyst, e.g. $AlCl_3$, $SnCl_4$, $FeCl_3$, etc. at a typical temperature of 0° C. to ambient, to form Compound III.

Compound III in turn is subjected to a selective reduction in a conventional manner with borane-tetrahydrofuran complex at a temperature of −30° C. to 0° C. for a time of 1 minute to 60 minutes to provide Compound II where R is H.

Compound IV is prepared generally in the manner described in British patent specification No. 1,481,866; British patent specification No. 1,538,775 and Ueno et al., *Journal of Medicinal Chemistry, Vol.* 19, No. 7, 941 (1976). For example, typically a phthalide of the formula

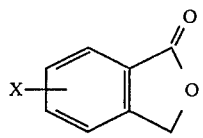
(VI)

is condensed under conventional conditions, e.g. by heating with a phenol of the formula

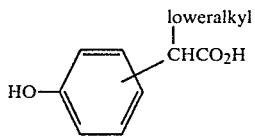
(VII)

to yield compound VIII of the formula

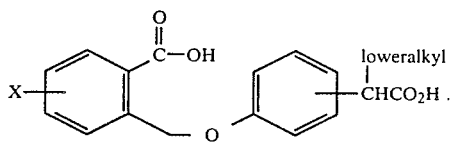
(VIII)

The resulting Compound VIII is then cyclized with a conventional cyclization agent, e.g. polyphosphoric ester from $P_2O_5$ and ethanol, polyphosphoric acid from $H_3PO_4$ and $P_2O_5$, etc. to form Compound IV. Compound IV is subjected to reduction as described to form Compound II where R is lower alkyl.

Compound II is reacted with a lower alkyl sulfonyl halide, e.g. methanesulfonyl chloride, in an anhydrous solvent, such as pyridine, at a temperature of −30° C. to 25° C. for 1 to 60 minutes to form a methane sulfonate of the formula

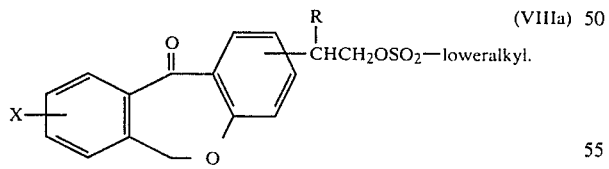
(VIIIa)

Compound VIIIa in turn is reacted with a compound having the formula H—$R^4$, where $R^4$ is selected from

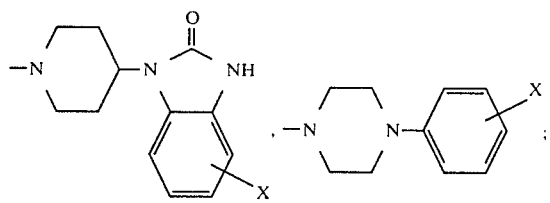

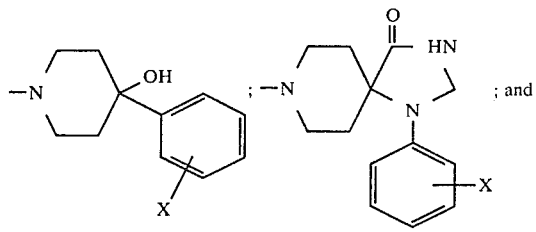
-continued

to form Compound I of the invention where $R_1$ is $R_4$. The reaction is carried out under conventional substitution reaction conditions, typically in the presence of a polar anhydrous solvent, e.g. methanol, ethanol, propanol, or a suitable mixture of such solvents, a base, such as for example $K_2CO_3$, at a temperature of ambient temperature to reflux for 1 to 48 hours.

B. Where R4 is

an alternative procedure involves selection of Compound IX having the formula

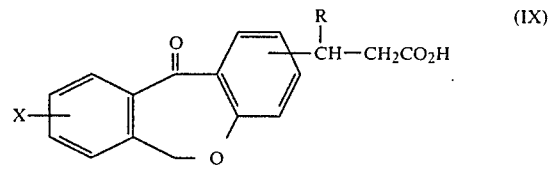
(IX)

Compound IX is prepared by reacting an ester of the formula (X),

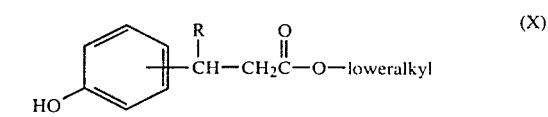
(X)

with a bromotoluate of the formula

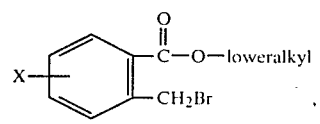
(XI)

under conventional substitution reaction conditions, in the presence of a base, e.g. $K_2CO_3$, to form Compound XII of the formula

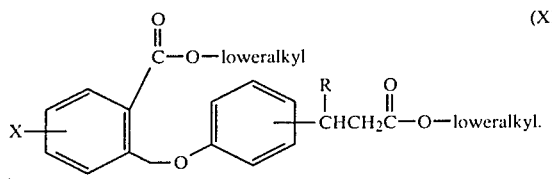

compound XII is then hydrolyzed to form the corresponding acid,

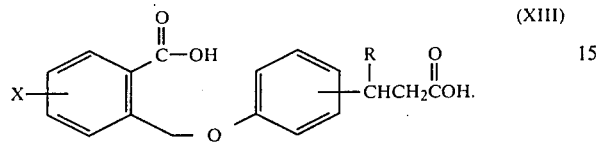

Compound XIII is then condensed in a conventional manner with a conventional condensing agent, e.g. $H_2SO_4$, polyphosphoric ester from $P_2O_5$ and ethanol, polyphosphoric acid from $H_3PO_4$ and $P_2O_5$, trifluoroacetic anhydride, etc. to form Compound IX.

Compound IX is converted to a mixed acid anhydride XIV in a conventional manner, e.g. by reaction with triethylamine and ethyl chloroformate in acetone at a temperature of $-10°$ to $+10°$ C. from 0.5 to 6 hours,

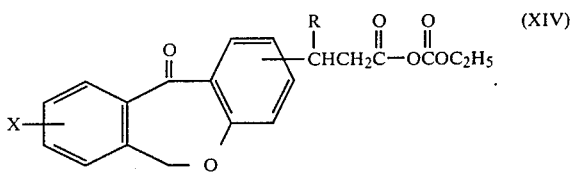

Compound XIV in turn is reacted with an azide, e.g., $NaN_3$, in a conventional manner in a water as the solvent, at a temperature of 0° to 5° C. for 0.1 to 2 hours to form azide XV,

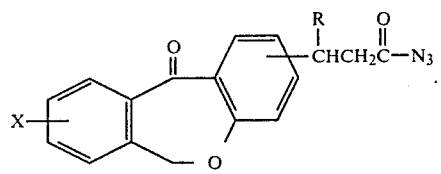

Compound XV in turn is subjected to a conventional Curtius type rearrangement reaction, e.g. heating with toluene at 50° to 120° C. until evolution of gas ceases to form an isocyanate of the formula

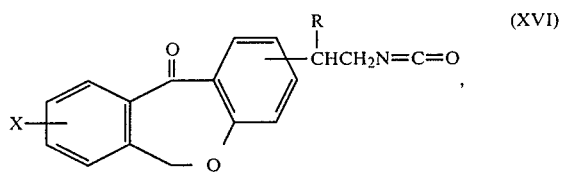

which is hydrolyzed in a conventional manner, e.g. refluxing of Compound XVI with 20% hydrochloric acid for 1 to 24 hours to form Compound I where $R_1$ is $-NH_2$.

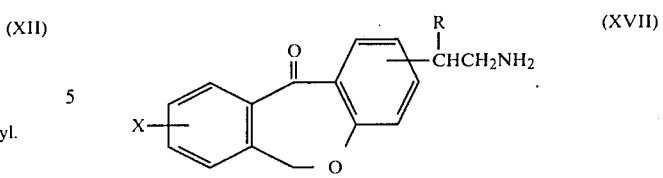

The N-alkyl or N-acyl derivatives of Compound XVII are prepared in a conventional manner, as for example by reaction with a lower alkyl halide or a cycloalkyl halide or an acylhalide of the formula

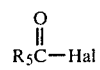

where Hal is a halogen selected from F, Cl, Br and I and $R_5$ is lower alkyl, or cycloalkylloweralkyl, whereby a mono- or bi-substituted compound of the invention, Compound XVIII is obtained,

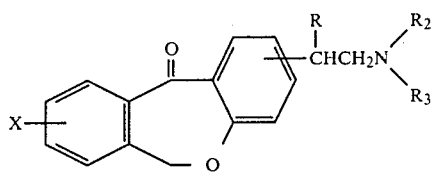

where at least $R_2$ or $R_3$ is lower alkyl, cycloalkyl or acyl of the formula

Alternatively N-alkyl derivatives of Compound XVII are prepared in a conventional manner, as for example by reaction of a lower alkylamine, e.g. methylamine, and Compound VIIIa to form Compound I where $R_1$ is $NHCH_3$,

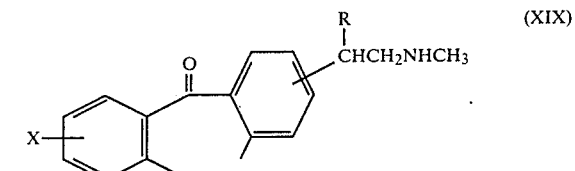

or by reductive alkylation of Compound XVII, as for example by reaction of formaldehyde and Compound XVII in the presence of a suitable reducing reagent such as sodium cyanoborohydride to form Compound I where $R_1$ is $N(CH_3)_2$,

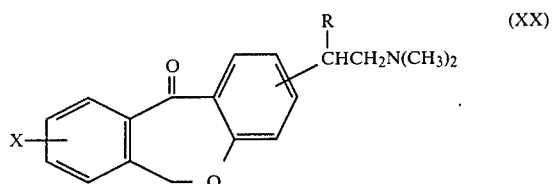

Compounds of the present invention are useful as analgesic agents due to their ability to alleviate pain in mammals. The activity of the compounds is demonstrated in the 2-phenyl-1,4-benzoquinone-induced writhing test in mice, a standard assay for analgesia [Proc. Soc. Exptl. Biol. Med., 95, 729 (1957)].

The analgesic activity of some of the compounds expressed in a dosage of the compounds which exhibit 50% inhibition ($ED_{50}$) of writhing is given in Table I.

TABLE I

| Compound | Oral Dose in mg/kg of body weight | % Inhibition |
|---|---|---|
| 2-(6,11-dihydro-11-oxodibenz-[b,e]oxepin-2-yl)ethylamine hydrochloride | 7.4** | 50 |
| 2-(6,11-dihydro-11-oxodibenz-[b,e]oxepin-2-yl)-N,N—dimethylethyl-amine hydrochloride | 25* | 66 |
| 2-(6,11-dihydro-11-oxodibenz[b,e]oxepin-2-yl-N—methyl ethylamine hydrochloride | 9.8** | 50 |
| 4-(2-keto-1-benzimidazolinyl)-1-[2-(6,11-dihydro-1-oxodibenz[b,e]oxepin-2-yl)ethyl]piperidine | 22.7** | 50 |
| 1-[2-(6,11-dihydro-11-oxodibenz[b,e]oxepin-2-yl)ethyl]-4-phenyl piperazine | 25** | 50 |
| 8-[2-(6,11-dihydro-11-oxodibenz[b,e]oxepin-2-yl)ethyl]-1-phenyl-1,3,8-triazaspiro-[4,5]-decan-4-one hydrochloride monohydrate | 8.4** | 50 |
| propoxyphene | 3.9* | 50 |

*subcutaneously
**$ED_{50}$

Effective amounts of the compounds of the present invention may be administered to a subject by one of various methods, for example, orally as in capsules or tablets, parenterally in the form of sterile solutions or suspensions, and in some cases intravenously in the form of sterile solutions. The compounds of the invention, while effective themselves, may be formulated and administered in the form of their pharmaceutically acceptable acid addition salts for purposes of stability, convenience of crystallization, increased solubility and the like.

Preferred pharmaceutically acceptable acid addition salts include those derived from inorganic acids such as hydrochloric hydrobromic, sulfuric, nitric, phosphoric, perchloric acids and the like as well as organic acids such as tartaric, citric, succinic, maleic, fumaric acids and the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the substituted alkyl amine 6,11-dihydro-11-oxodibenz[b,e]oxepin derivatives of the invention, the active ingredient, but may be varied depending upon the particular form and may conveniently be between 4% to about 70% of the weight of the unit. The amount of the compound present in such compositions is such that a suitable dosage will be obtained. Preferred compositions and preparations according to the present invention are prepared so that an oral dosage unit form contains between 5.0–300 milligrams of the substituted alkyl amine 6,11-dihydro-11-oxodibenz[b,e]oxepin derivatives of the invention.

The tablets, pills, capsules, troches and the like may also contain the following adjuvants: a binder such as microcrystalline cellulose, gum tragacanth or gelatin; an excipient such as starch or lactose, a disintegrating agent such as alginic acid, Primogel, corn starch and the like; a lubricant such as magnesium stearate of Sterotex; a glidant such as colloidal silicon dioxide; and a sweetening agent such as sucrose or saccharin may be added or a flavoring agent such as peppermint, methyl salicylate or orange flavoring. When the dosage unit form is a capsule, it may contain, in addition to material of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution of suspension. These preparations should contain at least 0.1% of the substituted alkyl amine 6,11-dihydro-11-oxodibenz[b,e]oxepin derivatives of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the substituted alkyl amine 6,11-dihydro-11-oxodibenz[b,e]oxepin derivatives of the invention.

The solutions or suspensions may also include the following adjuvants: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid, buffers such as acetates, citrates or phosphates and agents for the adjustment of tonicity such as sodium chloride or dextrose. The parenteral preparations can be enclosed in ampules, disposable syringes or multiple dose vials made of glass or plastic.

The following examples are for illustrative purposes and are not to be construed as limiting the invention disclosed herein. All temperatures are given in degrees centigrade.

EXAMPLE 1

2-(6,11-Dihydro-11-oxodibenz[b,e]oxepin-2-yl)ethanol methanesulfonate

A stirred chilled (−5° C.) solution of 2-(6,11-dihydro-11-oxodibenz[b,e]oxepin-2-yl)ethanol (5.08 g, 0.02 mol) and anhydrous pyridine (28 ml) was treated over 60 seconds with methanesulfonyl chloride (2.74 g, 0.024 mol). A mild exotherm was noted and a precipitate separated with continued cooling and stirring for 15 minutes after addition of the methanesulfonyl chloride was completed. Additional methanesulfonyl chloride (1.37 g, 0.012 mol) was added over 30 seconds and after stirring for 15 minutes the cooling bath was removed. After stirring 2 hours at ambient temperature, the mixture was decanted into 400 ml of ice cold water. The aqueous phase was decanted and the residual oil was stirred with water (300 ml). The water was decanted and the residual semisolid was triturated with ether. The resultant solid was collected, washed with ether and dried in vacuo to afford 4.92 g of crude material. Recrystallization from acetonitrile (15 ml) afforded 2.60 g (39.1%) of crystals, m.p. 108°–110° C.

ANALYSIS: Calculated for $C_{17}H_{16}O_5S$: 61.43%C; 4.85%H; Found: 61.59%C; 4.86%H

EXAMPLE 2

4-(2-Keto-1-benzimidazolinyl)-1-[2-(6,11-dihydro-11-oxodibenz [b,e]oxepin-2-yl)ethyl]piperidine A mixture of 5 g (0.023 m) of 4-(2-keto-1-benzimidazolinyl)piperidine, 7.65 g (0.023 m) of 2-(6,11-dihydro-11-oxodibenz[b,e]oxepin-2-yl)ethanol methanesulfonate of Example 1 and 3.17 g (0.023 m) of $K_2CO_3$ in 30 ml of absolute ethanol and 60 ml of methanol was refluxed overnight (about 16 hours). The reaction mixture was diluted with 800 ml of ethyl acetate, filtered and evaporated in vacuo. The residue was recrystallized from methanol to give after drying at 100° C. in vacuo, 5.78 g (56%) of 4-(2-keto-1-benzimidazolinyl)-1-[2-(6,11-dihydro-11-oxodibenz[b,e]oxepin-2-yl)ethyl]piperidine, m.p. 116°–120° C.

ANALYSIS: Calculated for $C_{28}H_{27}N_3O_3$: 74.15%C; 6.00%H; 9.26%N; Found: 74.32% C; 6.20%H; 9.22%N

EXAMPLE 3

1-[2-(6,11-Dihydro-11-oxodibenz[b,e]oxepin-2-yl)ethyl]-4-phenylpiperazine

A mixture of 6.3 g (0.039 m) of N-phenylpiperazine, 4.32 g (0.013 m) of 2-(6,11-dihydro-11-oxodibenz[b,e]oxepin-2-yl)ethanol methanesulfonate of Example 1 and 1.79 g (0.013 m) of $K_2CO_3$ in 50 ml of MeOH was refluxed overnight. The reaction mixture was poured into water, extracted with $CH_2Cl_2$, dried ($Na_2SO_4$), filtered and evaporated to give the crude product (6.5 (g). Two recrystallizations from absolute ethanol gave 1.63 g (32%) of crystals of 1-[2-(6,11-dihydro-11-oxodibenz[b,e]oxepin-2-yl)ethyl]-4-phenylpiperazine, m.p. 107°–108° C.

ANALYSIS: Calculated for $C_{26}H_{26}N_2O_2$: 78.36%C; 6.58%H; 7.03%N; Found: 78.17%C; 6.60%H; 6.83%N

EXAMPLE 4

4-(4-Chlorophenyl)-1-[2-(6,11-dihydro-11-oxodibenz[b,e]oxepin-2-yl)ethyl]-4-hydroxypiperidine A mixture of 3 g (0.014 m) of 4-(4-chlorophenyl)-4-hydroxypiperidine, 4.65 g (0.014 m) of 2-(6,11-dihydro-11-oxo-dibenz[b,e]oxepin-2-yl)ethanol methanesulfonate of Example 1, 1.96 g (0.014 m), of $K_2CO_3$, 30 ml of methanol and 30 ml of absolute ethanol was refluxed overnight. The yellow reaction mixture was filtered and evaporated. The residue was partitioned between ethyl acetate and water. The organic phase was dried ($Na_2SO_4$), filtered and evaporated to afford a solid. Trituration with ether gave 2.17 g (35%) of 4-(4-chlorophenyl)-1-[2-(6,11-dihydro-11-oxodibenz[b,e]oxepin-2-yl)ethyl]-4-hydroxypiperidine, m.p. 151°–153° C.

STRUCTURE: Calculated for $C_{27}H_{26}ClNO_3$: 72.39%C; 5.85%H; 3.13%N; Found: 72.20%C; 5.98%H; 2.95%N

EXAMPLE 5

8-[2-(6,11-Dihydro-11-oxodibenz[b,e]oxepin-2-yl)ethyl]-1-phenyl-1,3,8-triazaspiro[4,5]-decan-4-one hydrochloride monohydrate A mixture of 5 g (0.022 m) of 1-phenyl-1,3,8-triazaspiro[4,5]-decan-4-one (92% pure), 6.08 g (0.0183 m) of 2-(6,11-dihydro-11-oxodibenz[b,e]oxepin-2-yl)ethanol methanesulfonate of Example 1, and 2.5 g (0.0183 m) of $K_2CO_3$ in 60 ml of ethanol and 60 ml of methanol was refluxed for two days. Ethyl acetate was added to the reaction mixture and the salts were filtered off. The solvents were evaporated and the residue was dissolved in $CH_2Cl_2$, dried ($Na_2SO_4$), filtered and evaporated. The crude solid was triturated with hexane and filtered giving 7 g of crude product. The material was chromatographed on alumina and the product was eluted with 20% methanol in ether. The isolated product was dissolved in absolute ethanol and ethereal HCl added. On further addition of ether, a crystalline precipitate formed to give 2.39 g (25%) of 8-[2-(6,11-dihydro-11-oxodibenz[b,e]oxepin-2-yl)ethyl]-1-phenyl-1,3,8-triazaspiro[4,5]decan-4-one hydrochloride monohydrate, m.p. 192°–198° C. (sintered at 185° C.).

ANALYSIS: Calculated for $C_{29}H_{29}N_3O_3.HCl.H_2O$: 66.72%C; 6.17%H; 8.05%N; Found: 66.37%C; 5.80%H; 8.45%N

EXAMPLE 6 a. 4-(2-carboxybenzyloxy)phenylpropanoic acid

A mixture of 22.00 g (0.11 mole) of ethyl 3-(4-hydroxyphenyl) propionate, 27.44 g (0.11 mole) of ethyl α-bromo-o-toluate, 62.35 g (0.45 mole) of potassium carbonate, 450 ml of 2-butanone and 2.0 g of sodium iodide was refluxed for 17 hours. The reaction was cooled, the salts are filtered and washed with ether, the combined filtrate was concentrated in vacuo and the resulting oil was dissolved in ether. Washing with water, 5% NaOH, drying ($Na_2SO_4$), filtration and concentration in vacuo provided 20.57 g of an oil. The oil was refluxed with 71.82 g (1.28 mole) of potassium hydroxide, 358 ml of 95% ethanol and 36 ml water for 17 hours. The solution was cooled, the solvent removed in vacuo and the semisolid residue was dissolved in water and extracted with ether. The aqueous layer was acidified to pH 2 with concentrated HCl and the resulting precipitate was filtered, washed with acetonitrile and dried. Recrystallization from ethanol-water yielded 7.21 g (42% yield) of 4-(2-carboxybenzyloxy)phenylpropanoic acid, m.p. 176°–178° C.

ANALYSIS: Calculated: 67.98%C; 5.37%H; Found: 67.76%C; 5.37%H b. 6,11-Dihydro-11-oxodibenz[b,e]oxepin-2-propanoic acid A stirred suspension of 4-(2-carboxybenzyloxy)-phenylpropanoic acid (47.14 g, 0.157 mol) and dichloromethane (500 ml) was treated over 30 seconds with trifluoroacetic anhydride (75.61 g, 0.36 mol). The solid material slowly dissolved. The solution was heated 6 hours under reflux with exclusion of moisture. The cooled solution was treated with water (100 ml) and stirred 20 minutes at ambient temperature (mild exotherm). The mixture was strongly acidified with 5% hydrochloric acid and thoroughly agitated. The organic phase was washed with water (200 ml), dried ($Na_2SO_4$) and evaporated to dryness. Recrystallization from 65 ml of isopropanol afforded 35.3 g (79.6%) of 6,11-dihydro-11-oxodibenz[b,e]oxepin-2-propanoic acid, m.p. 138.5°–139.5° C. The compound appeared pure and chromatographically identical with material which had previously been prepared according to procedure 6C below except that it is postulated that the product exists in two polymorphic forms and interconversion by partial melting followed by solidification to afford the higher melting form occurs at 128°–130° C.

c. 6,11-dihydro-11-oxodibenz[b,e]oxepin-2-propanoic acid

Phosphorus pentoxide (10.4 g, 0.073 mole) was cautiously added to 7.4 ml of absolute ethanol under a nitrogen atmosphere and stirred at 110° C. for 1 hour; 53.1 ml of sulfolane was added and the temperature adjusted to 85° C. After adding 4-(2-carboxybenzyloxy)phenylpropanoic acid of Example 6a (5.0 g, 0.017 mole), the reaction was stirred at 85° C. for 3.5 hours. The mixture was poured into 1 liter of ice water, made basic by addition of NaOH pellets, extracted with toluene and the aqueous phase was then acidified with concentrated HCl. The resulting precipitate was filtered, triturated with isopropanol and dried giving 3.22 g of 6,11-dihydro-11-oxodibenz[b,e]oxepin-2-propanoic acid (68% yield), m.p. 128°–130° C.

ANALYSIS: Calculated: 72.32%C; 4.99%H; Found: 72.23%C; 4.97%H d. 2-(6,11-Dihydro-11-oxodibenz[b,e]oxepin-2-yl)ethylamine hydrochloride To a suspension of 10 g (0.035 m) of 6,11-dihydro-11-oxodibenz[b,e]oxepin-2-propanoic acid of Example 6b in 25 ml of H$_2$O, sufficient acetone (approximately 100 ml) was added to form a solution. The solution was cooled in an ice-salt bath and 4.05 g (0.04 m) of triethylamine in 100 ml of acetone was added dropwise maintaining temperature between 0°–1° C. A solution of 4.95 g (0.046 m) of ethyl chloroformate in 25 ml of acetone was added slowly. The mixture was stirred for 30 minutes at 0° C. A solution of 3.46 g (0.05 m) of NaN$_3$ in 25 ml of H$_2$O was added dropwise maintaining a temperature of 0° C. for one hour. The mixture was poured into an excess of ice water. The oil which separated was extracted into ether and the combined ether extracts were dried (Na$_2$SO$_4$), filtered and evaporated to give the acylazide as an oil. The azide was dissolved in 50 ml of anhydrous toluene. The toluene solution was heated (steam bath) until nitrogen evolution ceased. Removal of toluene in vacuo afforded the isocyanate as an oil. A mixture of the isocyanate and 90 ml of 20% aqueous HCl was refluxed 9 hours. The reaction mixture was evaporated and the residue was dissolved in water. The solution was made strongly alkaline with 10% NaOH. The oil which separated was extracted into ether and the combined ether extracts were dried (Na$_2$SO$_4$) and filtered. Ethereal HCl was added to the filtrate and the crystalline precipitate was collected to give 8 g (78%) of 2-(6,11-dihydro-11-oxodibenz[b,e]oxepin-2-yl)ethylamine hydrochloride, m.p. 189°–191° C.

ANALYSIS: Calculated for C$_{16}$H$_{15}$NO$_2$.HCl: 66.32%C; 5.57%H; 4.83%N; Found: 66.16%C; 5.47%H; 5.15%N

EXAMPLE 7

2-(6,11-Dihydro-11-oxodibenz[b,e]oxepin-2-yl)-N,N-dimethylethylamine hydrochloride To a solution of 2.8 g (0.011 m) of 2-(6,11-dihydro-11-oxodibenz[b,e]oxepin-2-yl)ethylamine of Example 6 in 60 ml of acetonitrile and 2.7 ml of 37% aqueous formaldehyde (0.1 m), 2.05 g (0.033 m) of NaBH$_3$CN was added. There was a slightly exothermic reaction. Glacial acetic acid (2 ml) was added over 10 minutes and the reaction was stirred at ambient temperature for 2 hours. An additional 2 ml of glacial acetic acid was added and stirring was continued for 30 minutes. The solvent was evaporated under reduced pressure and the residue was treated with 60 ml of 2N KOH. The resulting mixture was extracted three times with ether. The combined ether extracts were washed with 60 ml of 0.5N KOH and then extracted three times with 1N HCl. The aqueous acidic extracts were combined and neutralized with solid KOH and then extracted with ether. The dried (Na$_2$SO$_4$) organic phase was filtered and ethereal HCl was added to precipitate 2-(6,11-dihydro-11-oxodibenz[b,e]oxepin-2-yl)-N,N-dimethylethylamine hydrochloride, 1.4 g (40%), m.p. 175°–176° C.

ANALYSIS: Calculated for C$_{18}$H$_{19}$NO$_2$.HCl: 68.03%C; 6.34%H; 4.41%N; Found: 68.19%C; 6.31%H; 4.29%N

EXAMPLE 8

2-(6,11-Dihydro-11-oxodibenz[b,e]oxepin-2-yl)-N-methylethylamine hydrochloride

A mixture of 1.5 g (0.0045 m) of 2-(6,11-dihydro-11-oxodibenz[b,e]oxepin-2-yl)ethanol methanesulfonate of Example 1, 20 ml of absolute ethanol and 20 ml of CH$_3$NH$_2$ was charged into a stainless steel Paar bomb. The bomb was placed in 60° C. oil bath overnight. The solvent was evaporated and the residue was extracted with ether. The ether extract was washed with 10% Na$_2$CO$_3$ and water, dried (Na$_2$SO$_4$), filtered and ethereal hydrogen chloride was added to afford 2-(6,11-dihydro-11-oxodibenz[b,e]oxepin-2-yl)-N-methylethylamine hydrochloride, 1.23 g (90%) m.p. 175°–178° C.

ANALYSIS: Calculated for C$_{17}$H$_{17}$NO$_2$.HCl: 67.15%C; 5.97%H; 4.60%N; Found: 67.14%C; 6.03%H; 4.41%N

EXAMPLE 9

N-(2-(6,11-Dihydro-11-oxodibenz[b,e]oxepin-2-yl)ethyl)methanesulfonamide

To a solution of 3.5 g (0.014 m), of 2-(6,11-dihydro-11-oxodibenz[b,e]oxepin-2-yl)ethylamine of Example 6 and 1.4 g (0.014 m) of triethylamine in 50 ml of CH$_2$Cl$_2$, 1.6 g (0.014 m) of methanesulfonyl chloride was added dropwise maintaining the temperature between 15°–20° C. The mixture was stirred 45 minutes, then poured into water. The CH$_2$Cl$_2$ layer was separated, washed with water, dried (Na$_2$SO$_4$), filtered and evaporated to give a foamy solid. Recrystallization from approximately 40 ml of toluene gave 2.27 g (49%) of N-(2-(6,11-dihydro-11-oxodibenz[b,e]oxepin-2-yl)ethyl)methanesulfonamide, m.p. 104°–106° C.

ANALYSIS: Calculated for C$_{17}$H$_{17}$NO$_4$S: 61.61%C; 5.17%H; 4.23%N; Found: 61.88%C; 5.11%H; 4.11%N

We claim:

1. A compound having the formula

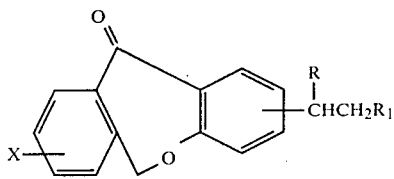

where X is hydrogen, halogen, lower alkoxy, lower alkyl, nitro amino, hydroxyl and $CF_3$; R is hydrogen, and lower alkyl; $R_1$ is

where $R_2$ and $R_3$ are the same or different and are hydrogen, lower alkyl, mesyl, and cycloalkylloweralkyl possessing a carbocyclic ring of 3 to 7 carbon atoms;

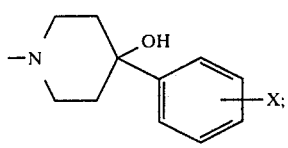

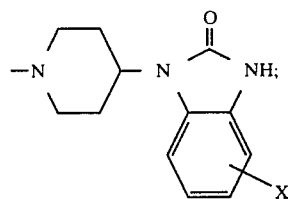

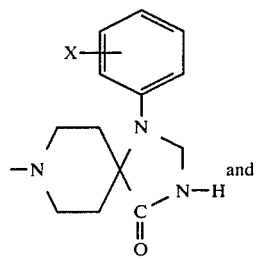

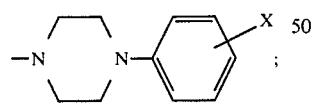

and the pharmaceutically acceptable acid addition salts thereof.

2. The compound as defined in claim 1 which is 4-(2-keto-1-benzimidazolinyl)-1-[2-(6,11-dihydro-11-oxodibenz[b,e]oxepin-2-yl)ethyl]piperidine or a pharmaceutically acceptable salt thereof.

3. The compound as defined in claim 1 which is 1-[2-(6,11-dihydro-11-oxidibenz[b,e]oxepin-2-yl)ethyl]-4-phenylpiperazine or a pharmaceutically acceptable salt thereof.

4. The compound as defined in claim 1 which is 4-(4-chlorophenyl)-1-[2-(6,11-dihydro-11-oxodibenz[b,e]oxepin-2-yl)ethyl]-4-hydroxypiperidine or a pharmaceutically acceptable salt thereof.

5. The compound as defined in claim 1 which is 8-[2-(6,11-dihydro-11-oxodibenz[b,e]oxepin-2-yl)ethyl]-1-phenyl-1,3,8-triazaspiro[4,5]-decan-4-one or a pharmaceutically acceptable salt thereof.

6. The compound as defined in claim 1 which is 2-(6,11-dihydro-11-oxodibenz[b,e]oxepin-2-yl)ethylamine or a pharmaceutically acceptable salt thereof.

7. The compound as defined in claim 1 which is 2-(6,11-dihydro-11-oxodibenz[b,e]oxepin-2-yl)-N,N-dimethylethylamine or a pharmaceutically acceptable salt thereof.

8. The compound as defined in claim 1 which is 2-(6,11-dihydro-11-oxodibenz[b,e]oxepin-2-yl)-N-methylethylamine or a pharmaceutically acceptable salt thereof.

9. The compound as defined in claim 1 which is N-{2-(6,11-dihydro-11-oxodibenz[b,e]oxepin-2-yl)ethyl}methane sulfonamide or a pharmaceutically acceptable salt thereof.

10. An analgesic composition which comprises an effective pain alleviating amount of a compound of the formula

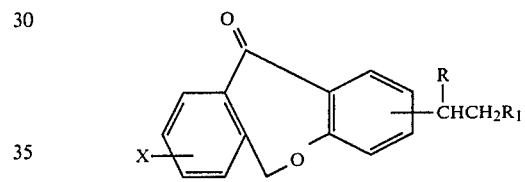

where X is hydrogen, halogen, lower alkoxy, lower alkyl, nitro amino, hydroxyl and $CF_3$; R is hydrogen, and lower alkyl; $R_1$ is

where $R_2$ and $R_3$ are the same or different and are hydrogen, lower alkyl, mesyl, and cycloalkylloweralkyl possessing a carbocylic ring of 3 to 7 carbon atoms;

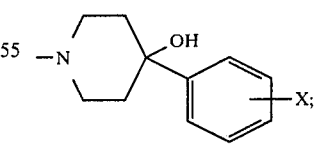

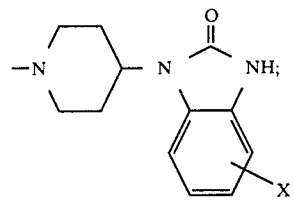

-continued

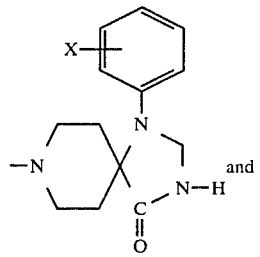
and

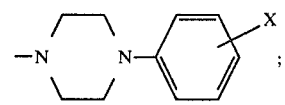

and the pharmaceutically acceptable acid addition salts thereof.

11. The analgesic composition as defined in claim 10 which comprises 4-(2-keto-1-benzimidazolinyl)-1-[2-(6,11-dihydro-11-oxodibenzo[b,e]oxepin-2-yl)ethyl]-piperidine or a pharmaceutically acceptable salt thereof.

12. The analgesic composition as defined in claim 10 which comprises 1-[2-(6,11-dihydro-11-oxidibenz[b,e]oxepin-2-yl)ethyl]-4-phenylpiperazine or a pharmaceutically acceptable salt thereof.

13. The analgesic composition as defined in claim 10 which comprises 4-(4-chlorophenyl)-1-[2-(6,11-dihydro-11-oxodibenz[b,e]oxepin-2-yl)ethyl]-4-hydroxypiperidine or a pharmaceutically acceptable salt thereof.

14. The analgesic composition as defined in claim 10 which comprises 8-[2-(6,11-dihydro-11-oxodibenz[b,e]oxepin-2-yl)ethyl]-1-phenyl-1,3,8-triazaspiro[4,5]-decan-4-one or a pharmaceutically acceptable salt thereof.

15. The analgesic composition as defined in claim 10 which comprises 2-(6,11-dihydro-11-oxodibenz[b,e]oxepin-2-yl)ethylamine or a pharmaceutically acceptable salt thereof.

16. The analgesic composition as defined in claim 10 which comprises 2-(6,11-dihydro-11-oxodibenz[b,e]oxepin-2-yl)-N,N-dimethylethylamine or a pharmaceutically acceptable salt thereof.

17. The analgesic composition as defined in claim 10 which comprises 2-(6,11-dihydro-11-oxodibenz[b,e]oxepin-2-yl)-N-methylethylamine or a pharmaceutically acceptable salt thereof.

18. The analgesic composition as defined in claim 10 which comprises N-{2-(6,11-dihydro-11-oxodibenz[b,e]oxepin-2-yl)ethyl}methane sulfonamide or a pharmaceutically acceptable salt thereof.

19. A method of alleviating pain in a mammal which comprises administering to a mammal an effective pain alleviating amount of a compound of the formula

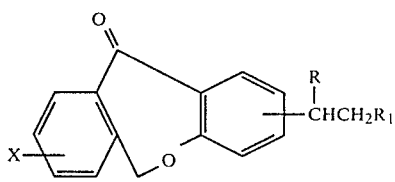

where X is hydrogen, halogen, lower alkoxy, lower alkyl, nitro amino, hydroxyl and CF$_3$; R is hydrogen, and lower alkyl, R$_1$ is

where R$_2$ and R$_3$ are the same or different and are hydrogen, lower alkyl, mesyl, and cycloalkylloweralkyl possessing a carbocyclic ring of 3 to 7 carbon atoms;

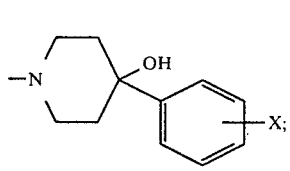

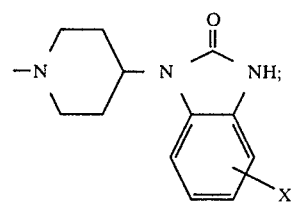

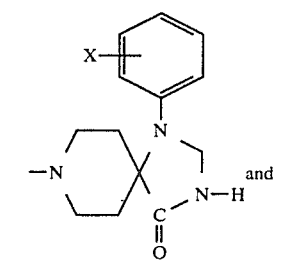
and

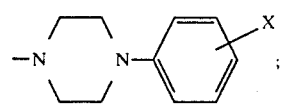

and the pharmaceutically acceptable acid addition salts thereof.

20. The method as defined in claim 19 wherein said compound is 4-(2-keto-1-benzimidazolinyl)-1-[2-(6,11-dihydro-11-oxodibenz[b,e]oxepin-2-yl)ethyl]piperidine or a pharmaceutically acceptable salt thereof.

21. The method as defined in claim 19 wherein said compound is 1-[2-(6,11-dihydro-11-oxidibenz[b,e]oxepin-2-yl)ethyl]-4-phenylpiperazine or a pharmaceutically acceptable salt thereof.

22. The method as defined in claim 19 wherein said compound is 4-(4-chlorophenyl)-1-[2-(6,11-dihydro-11-oxodibenz[b,e]oxepin-2-yl)ethyl]-4-hydroxypiperidine or a pharmaceutically acceptable salt thereof.

23. The method as defined in claim 19 wherein said compound is 8-[2-(6,11-dihydro-11-oxodibenz[b,e]oxepin-2-yl)ethyl]-1-phenyl-1,3,8-triazaspiro[4,5]-decan-4-one or a pharmaceutically acceptable salt thereof.

24. The method as defined in claim 19 wherein said compound is 2-(6,11-dihydro-11-oxodibenz[b,e]oxepin-2-yl)ethylamine or a pharmaceutically acceptable salt thereof.

25. The method as defined in claim 19 wherein said compound is 2-(6,11-dihydro-11-oxodibenz[b,e]oxepin-2-yl)-N,N-dimethylethylamine or a pharmaceutically acceptable salt thereof.

26. The method as defined in claim 19 wherein said compound is 2-(6,11-dihydro-11-oxodibenz[b,e]oxepin-2-yl)-N-methylethylamine or a pharmaceutically acceptable salt thereof.

27. The method as defined in claim 19 wherein said compound is N-{2-(6,11-dihydro-11-oxodibenz[b,e]oxepin-2-yl)ethyl}methane sulfonamide or a pharmaceutically acceptable salt thereof.

* * * * *